(12) United States Patent
Kayerød et al.

(10) Patent No.: US 6,634,498 B2
(45) Date of Patent: *Oct. 21, 2003

(54) READY-TO-USE URINARY CATHETER ASSEMBLY

(75) Inventors: Helle Kayerød, Copenhagen (DK); Allan Tanghøj, Kokkedal (DK); Ulrik Nøsted, Lyngby (DK); Jan Torstensen, Virum (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/754,535

(22) Filed: Jan. 4, 2001

(65) Prior Publication Data

US 2001/0001443 A1 May 24, 2001

Related U.S. Application Data

(62) Division of application No. 08/952,040, filed as application No. PCT/ES97/00056 on Mar. 10, 1997, now abandoned.

(30) Foreign Application Priority Data

Sep. 18, 1996 (DK) ................................. 1023/96
Nov. 1, 1996 (DK) ................................. 1224/96

(51) Int. Cl.⁷ ............................................... B65D 85/08
(52) U.S. Cl. ......................... 206/364; 206/210; 604/265
(58) Field of Search ................................ 206/210, 364, 206/438, 571; 604/265

(56) References Cited

U.S. PATENT DOCUMENTS 2,856,932 A    10/1958   Griffitts
3,035,691 A  *  5/1962   Rasmussen et al. ........ 206/364

(List continued on next page.)

FOREIGN PATENT DOCUMENTS

| CN | 1106744   | 8/1995 |
|----|-----------|--------|
| DE | 2 317 839 | 10/1974 |
| DK | 0932      | 1/1989 |
| EP | 0 217 771 | 4/1987 |
| EP | 0586324   | 3/1994 |
| EP | 0 586 327 | 3/1994 |
| EP | 0677299   | 10/1995 |
| EP | 0 677 299 | 10/1995 |
| EP | 0 680 895 | 11/1995 |
| EP | 0 685 179 | 12/1995 |
| EP | 0959930   | 12/1999 |
| GB | 1600963   | 10/1981 |
| GB | 2 284 764 | 6/1995 |
| JP | 55-12265  | 3/1980 |
| WO | 8606284   | 11/1986 |
| WO | 9406377   | 3/1994 |

(List continued on next page.)

OTHER PUBLICATIONS

"Intermittent self–catheterisation: research–based practice", Katherine N. Moore, British Journal of Nursing, 1995, vol. 4, No. 18, pp. 1057–1063.

"Annual Report 1998/1999", Coloplast, Financial Year: Oct. 1, 1998 –Sep. 30, 1999.

Primary Examiner—John G. Weiss
Assistant Examiner—Michael J. Fisher
(74) Attorney, Agent, or Firm—Jacobson Holman PLLC

(57) ABSTRACT

A urinary catheter assembly including a urinary catheter having on at least a part of its surface a hydrophilic surface layer intended to produce a low-friction surface character of the catheter by treatment with a liquid swelling medium during manufacture of the catheter assembly, and a catheter package having a cavity for accommodation of the catheter. The package includes a compartment having walls of a gas impermeable material and accommodating the liquid swelling medium and a catheter pretreated therewith for long time preservation of the low-friction surface character and provision of a ready-to-use catheter assembly.

21 Claims, 11 Drawing Sheets

U.S. PATENT DOCUMENTS

| | | | |
|---|---|---|---|
| 3,345,988 A | | 5/1965 | Vitello |
| 3,556,294 A | | 1/1971 | Walck et al. |
| 3,648,704 A | | 3/1972 | Jackson |
| 3,854,483 A | | 12/1974 | Powers |
| 3,861,395 A | | 1/1975 | Taniguchi |
| 3,898,993 A | | 8/1975 | Taniguchi |
| 3,930,580 A | * | 1/1976 | Bazell et al. ............... 206/364 |
| 3,934,721 A | | 1/1976 | Juster et al. |
| 3,967,728 A | * | 7/1976 | Gorden et al. .............. 206/364 |
| 3,978,983 A | | 9/1976 | Brezette |
| 4,119,094 A | | 10/1978 | Micklus et al. |
| 4,204,527 A | | 5/1980 | Wu et al. |
| 4,230,115 A | | 10/1980 | Walz, Jr. et al. |
| 4,269,310 A | * | 5/1981 | Uson .......................... 206/210 |
| 4,379,506 A | | 4/1983 | Davidson |
| 4,515,593 A | * | 5/1985 | Norton ....................... 604/265 |
| 4,585,666 A | | 4/1986 | Lambert |
| 4,754,877 A | | 7/1988 | Johansson et al. |
| 4,811,847 A | | 3/1989 | Reif et al. |
| 4,906,237 A | * | 3/1990 | Johansson et al. .......... 604/265 |
| 5,041,100 A | * | 8/1991 | Rowland et al. ............ 604/265 |
| 5,147,341 A | | 9/1992 | Starke et al. |
| 5,226,530 A | * | 7/1993 | Golden ....................... 206/210 |
| 5,242,428 A | | 9/1993 | Palestrant |
| 5,416,131 A | * | 5/1995 | Wolff et al. .................. 604/265 |
| 5,441,488 A | * | 8/1995 | Shimura et al. ............. 604/265 |
| 5,454,798 A | | 10/1995 | Kubalak et al. |
| 5,509,899 A | * | 4/1996 | Fan et al. .................... 604/265 |
| 5,531,715 A | * | 7/1996 | Engelson et al. ........... 604/265 |
| 5,642,593 A | | 7/1997 | Shieh |
| 5,702,754 A | | 12/1997 | Zhong |
| 6,059,107 A | * | 5/2000 | Nostad et al. ............... 206/364 |

FOREIGN PATENT DOCUMENTS

| | | |
|---|---|---|
| WO | 94/16747 | 8/1994 |
| WO | 96/30277 | 10/1996 |
| WO | 9726937 | 7/1997 |
| WO | 98/11932 | 3/1998 |
| WO | 98/58988 | 12/1998 |
| WO | 98/58989 | 12/1998 |
| WO | 98/58990 | 12/1998 |

* cited by examiner

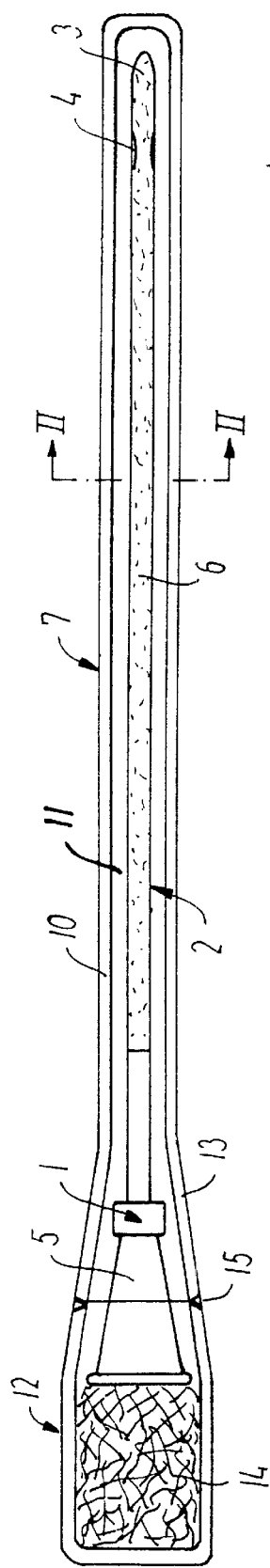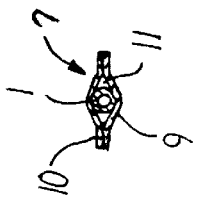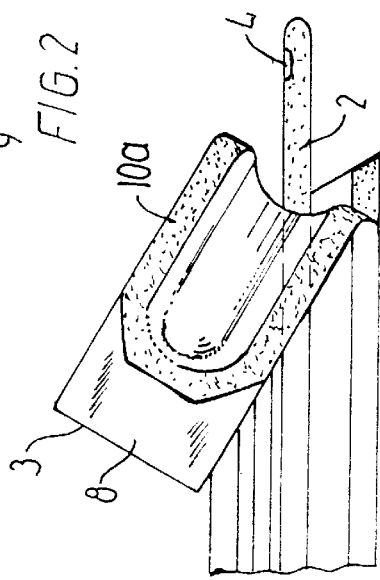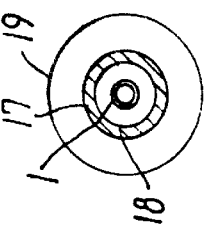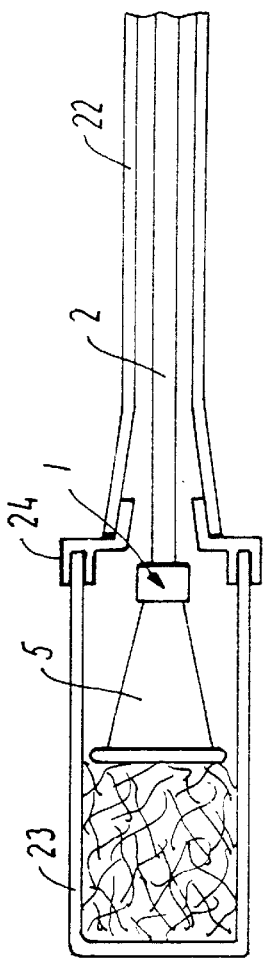

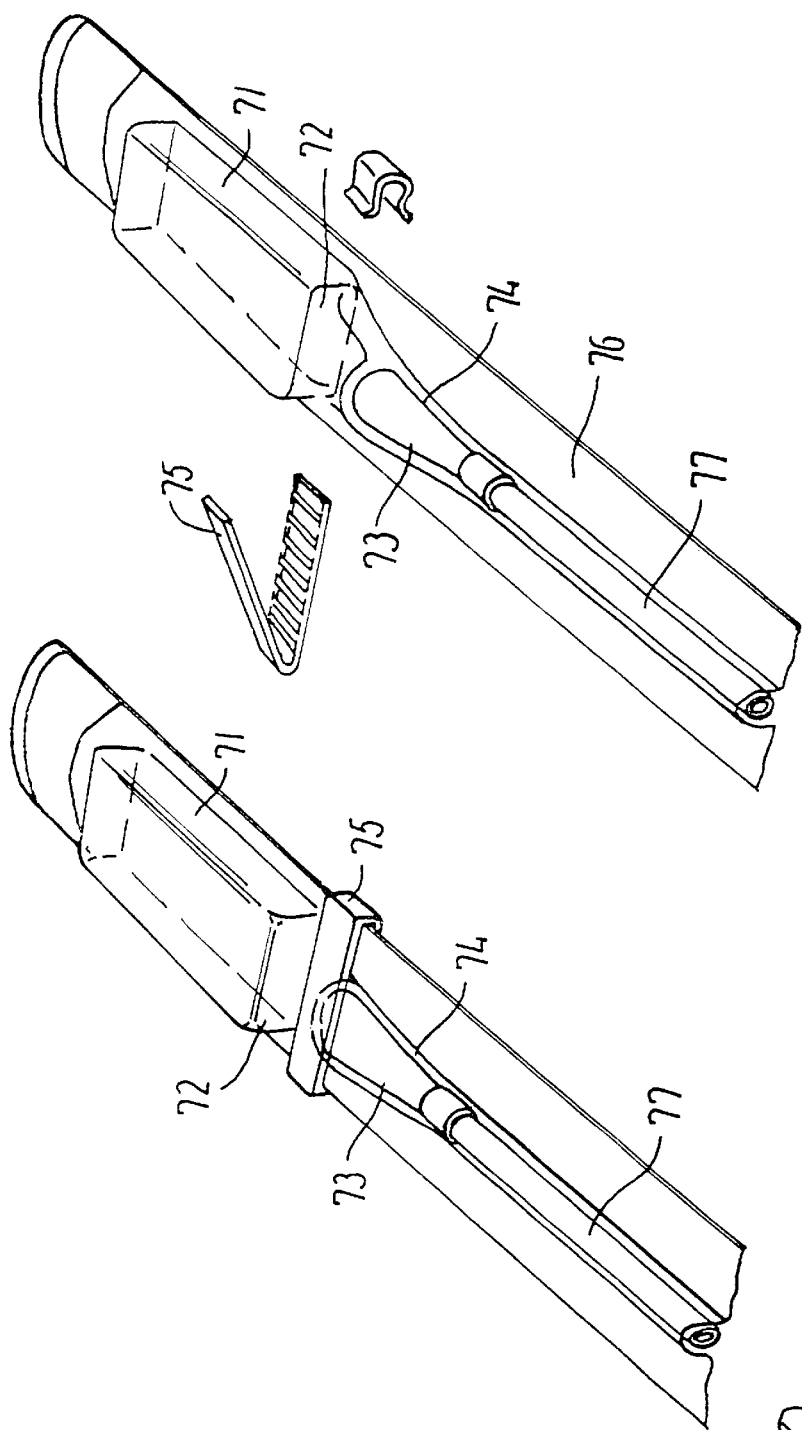

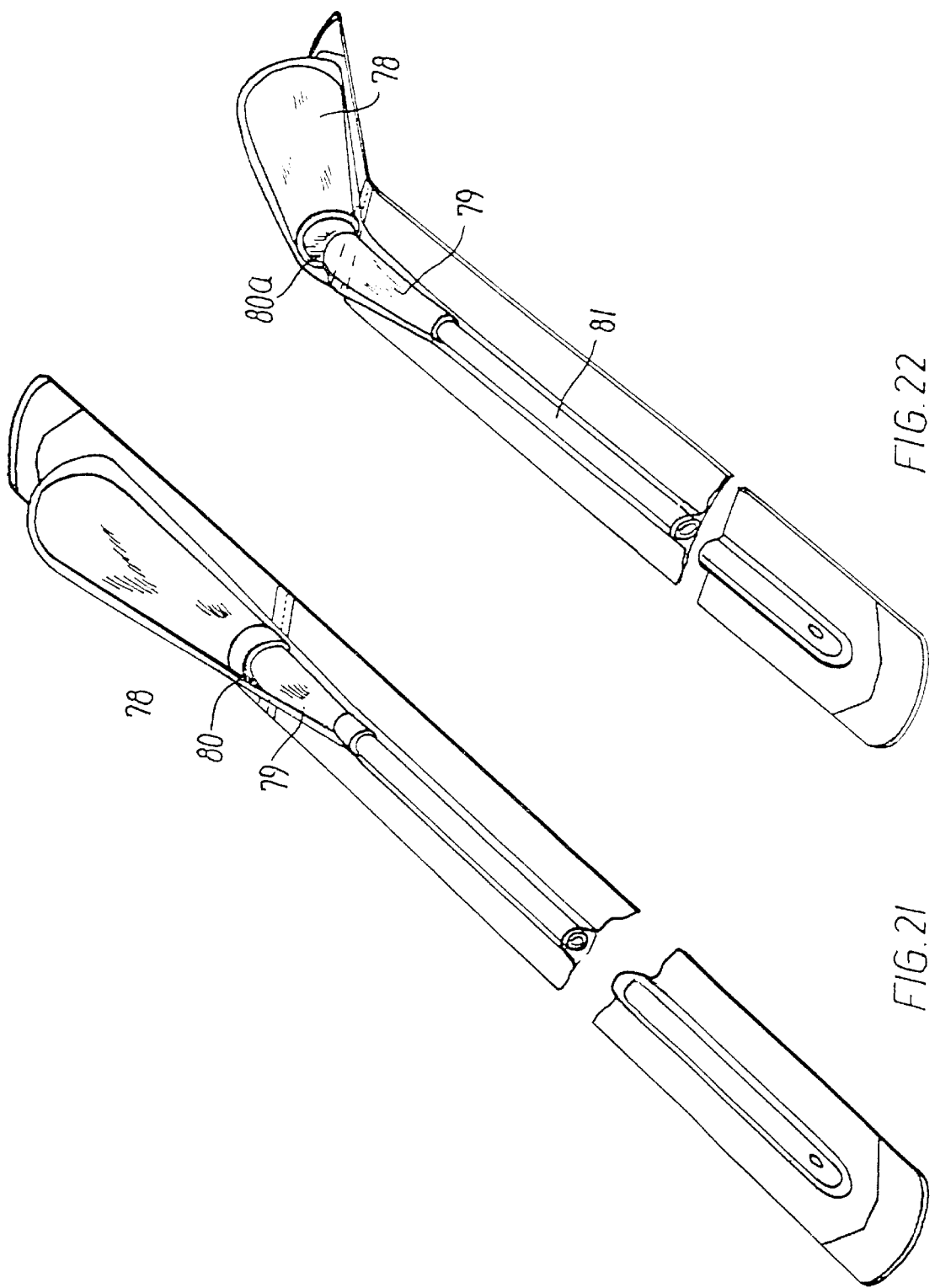

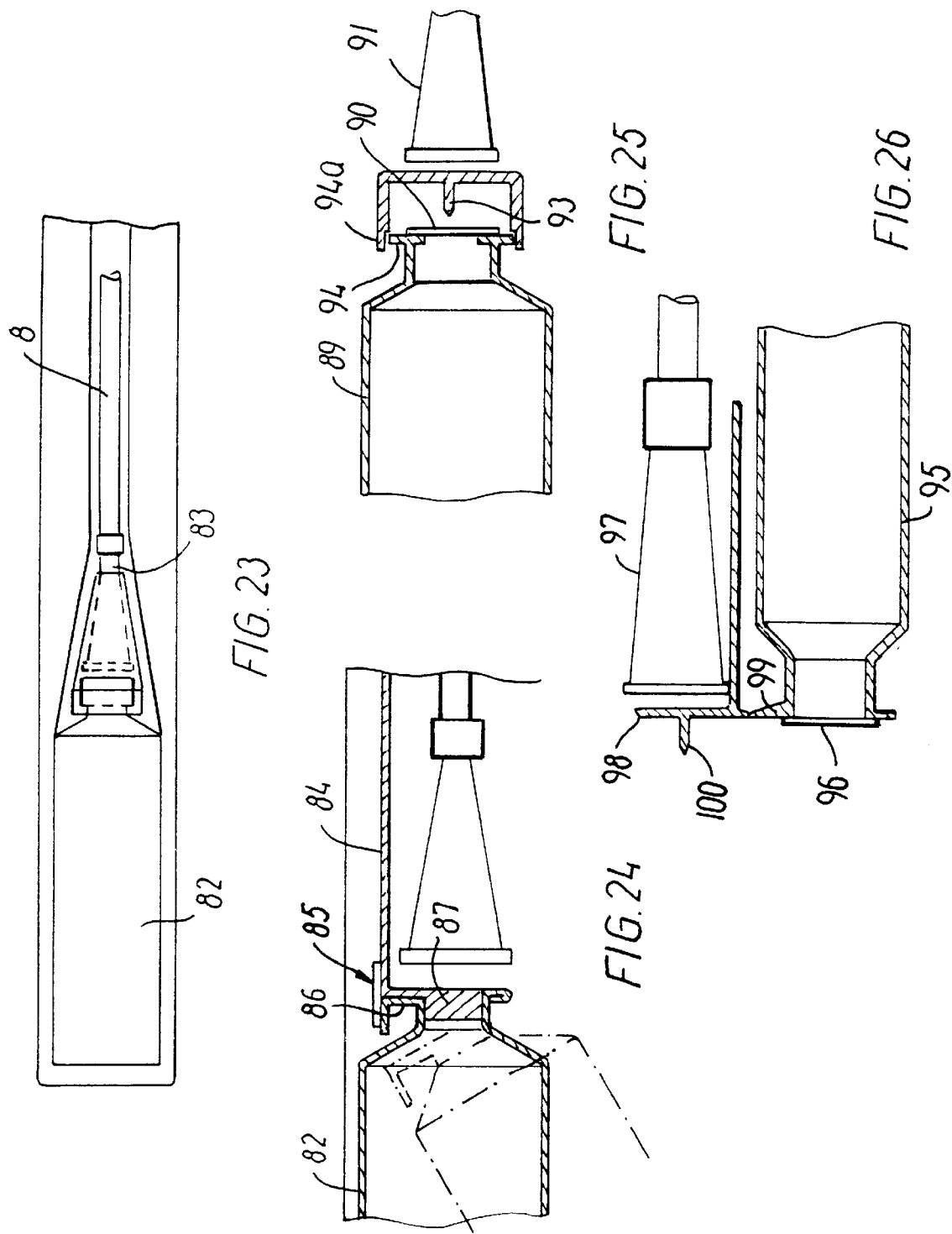

READY-TO-USE URINARY CATHETER ASSEMBLY

This is a divisional of application Ser. No. 08/952,040, filed Nov. 6, 1997, now abandoned, which is a 371 of PCT/ES97/00056, filed Mar. 10, 1997.

This invention relates to at least one urinary catheter assembly comprising a urinary catheter having on at least a part of its surface a hydrophilic surface layer intended to produce a low-friction surface of the catheter by treatment with a liquid swelling medium prior to use of the catheter and a catheter package having a cavity for accommodation of the catheter.

Urinary catheters of the kind to which the invention pertains are known, inter alia, from EP-A-0 217 771, EP-A-0 586 324 and WO 94/16747, whereas various forms of catheter packages are known from U.S. Pat. Nos. 3,035,691, 3,648,704, 3,967,728, 4,204,527, 4,269,310, 4,379,506, 5,454,798, GB-A-2,284,764, DE-A-2,317839, EP-A-0 677 299 and DK Design Registration No. 0932 1986.

U.S. Pat. Nos. 3,648,704, 3,967,728, 4,269,310, GB-A-2,284,764 and EP-A-0 677 299 disclose a conventional urinary catheter assembly comprising a catheter of the kind where prior to insertion of the catheter into the urethra the tip of the catheter is to be lubricated with a gel-like lubricant and a package where such a lubricant is accommodated in a rupturable pouch connected with or located within the package itself adjacent to the tip of the catheter or supplied together with the catheter package for connection therewith prior to use of the catheter.

An important feature of any urinary catheter used for intermittent catherisation of the bladder of an incontinent user is the ability of the catheter to slide easily through the urethra without exposing the urethral walls to any risk of damage. Catheters of the kind to which the inventions pertains have been developed to meet this need by imparting an extremely low friction character to at least the part of the surface of the catheter which is actually introduced into the urethra. The low friction surface character is obtained by incorporating into the relevant part of the catheter at least a hydrophilic surface layer, typically in the form of a coating, and exposing this layer or coating to contact with a liquid swelling medium immediately prior to use.

In order to maintain the low friction surface character during location of the catheter in the urethra and subsequent with drawal therefrom and hereby reduce stinging pain it is further known to incorporate an osmolality promoting agent, such as NaCl, in the hydrophilic coating.

When catheters of this kind are used directly by end users outside the medical environment of a hospital or a clinic, e.g. by or tetraplegic patients who often have a very poor dexterity, and therefore need a very simple insertion procedure, the most common liquid swelling medium used for preparation of the catheter immediately prior to use would be normal tap water.

In order to reduce the risk of infection inherent with the performance of intermittent catherisation of the bladder both the actual swelling medium used and the environment in which the catherisation is performed need, to be as clean and antiseptic as possible. Evidently, this need may be very difficult to meet in many daily life situations, as where catherisation must be performed outside the users normal daily environment, e.g. in public toilets, where neither the water supply nor the general state of cleanliness can be expected to be of a sufficiently high standard. Moreover, many disabled users have severe difficulties in entering available toilet rooms due to simple physical barriers like narrow access ways, stairs and the like.

On this background, it is the object of the invention to improve and facilitate the performance of intermittent urinary catherisation in any type of environment by providing a ready to use urinary catheter assembly comprising a catheter which can be withdrawn from its package and is prepared for direct insertion in the urethra and in a substantially sterile condition, whereby the general quality of life for users of intermittent catherisation would be greatly improved.

In order to meet this and other objects of the invention, as set forth in the following, a urinary catheter according to the invention is characterised in that the package includes a compartment having walls of a gas impermeable material, said compartment accommodating said liquid swelling medium for provision of a ready-to-use catheter assembly.

The term "gas impermeable" material should be understood in this context to mean any material that will be sufficiently tight against diffusion by evaporation of the actual liquid swelling medium for a period exceeding the recommended shelf life time of the catheter assembly which could be up to five years, typically 36 months.

In a first series of embodiments of the urinary catheter assembly of the invention the catheter package as a whole is made of a gas impermeable material and the compartment for the liquid swelling medium is in liquid flow communication with the cavity for accommodation of the catheter.

In one preferred embodiment of this kind the catheter package may be formed from two sheets of gas impermeable film material connected with each other by a gas impermeable joint defining said compartment and the cavity for accommodating the catheter.

Thereby, the preparation of the catheter with the liquid swelling medium prior to use can be made very simple by application of a pressure to the walls of the compartment, whereby the liquid swelling medium will be transferred to the cavity, which may have a cross section narrowly surrounding the catheter, to activate the hydrophilic surface layer of the catheter.

The compartment for the liquid swelling medium may be entirely integrated with the cavity for the catheter, whereby the hydrophilic surface layer of the catheter will be activated immediately after completion of the production process, when the swelling medium has been introduced in the package. The gas-impermeable walls of the package will then protect the activated coating from drying out and provide a long time preservation of the low friction surface characteristic of the catheter until the moment of actual use.

It may be preferred, however, to separate the compartment for the swelling medium from the catheter cavity and provide the liquid flow communication as a relatively narrow passage to confine the swelling medium in the compartment until activation of the hydrophilic surface coating of the catheter is required immediately prior to use of the catheter.

To achieve this the liquid swelling medium may advantageously be confined in a storage body arranged in said compartment and made of a material which is able to serve as a storage for the liquid swelling medium and can discharge therefore the swelling medium by a simple physical action such as the application of an external pressure or squeezing effect. Such a material may typically be a spongy material or an absorbing gel.

The joint between the two sheets of film material of the package may advantageously be a welded joint which may be formed to allow easy opening of the package for withdrawal of the prepared catheter.

Such a welded joint may comprise a part provided between said compartment and said cavity as a peelable joint permitting separation of said compartment from said cavity after transfer of said liquid swelling medium from said compartment to said cavity for withdrawal of the catheter from the package.

Alternatively, such a welded joint may comprise a part at the end of the package remote from said compartment providing a peel-off joint to separate said sheets from each other for withdrawal of said catheter from the package.

In other embodiments of the type in which the compartment for the swelling medium is in liquid flow communication with the catheter cavity the package may comprise a first generally tubular part defining said cavity to narrowly surround the catheter and a second generally tubular part defining said compartment.

Embodiments of this type are quite simple and cheap in production. Typically, the first and second tubular parts may be integrally formed from an elongate hose-like member, one end section of which is expanded to constitute said second tubular part.

In a second series of embodiments, the compartment for the swelling medium is separated from the cavity for accommodation of the catheter, and the swelling medium is confined in said compartment in a liquid state until the intended use of the catheter.

In one embodiment of this type, the compartment for the swelling medium may be formed by a container arranged around a proximal part of said catheter not provided with said hydrophilic layer, said catheter passing through said container via sealed openings, said catheter and said container being arranged in said package to allow said catheter to be drawn through said container by withdrawal of the catheter from the package.

In order to reduce the amount of liquid swelling medium required for activation of the hydrophilic surface coating of the catheter, the latter may advantageously be provided with means preventing said swelling medium from getting into contact with internal or external surface parts of the catheter not provided with said hydrophilic layer for an activation period during which said medium is applied to the surface part provided with said hydrophilic layer.

In the following, the invention will be explained in more detail by means of various embodiments illustrated in the accompanying drawings, in which FIGS. 1 and 2 are an upper plan view and a cross-sectional view, respectively, of a first embodiment of a urinary catheter assembly according to the invention;

FIG. 3 shows a modification of the embodiment in FIGS. 1 and 2;

FIGS. 4 and 5 are a side view and a cross-sectional view, respectively, of a second embodiment;

FIG. 6 shows a modification of the embodiment in FIGS. 4 and 5;

FIGS. 14 to 28 are representations of a number of further embodiments of the urinary catheter assembly of the invention.

Figure 7:
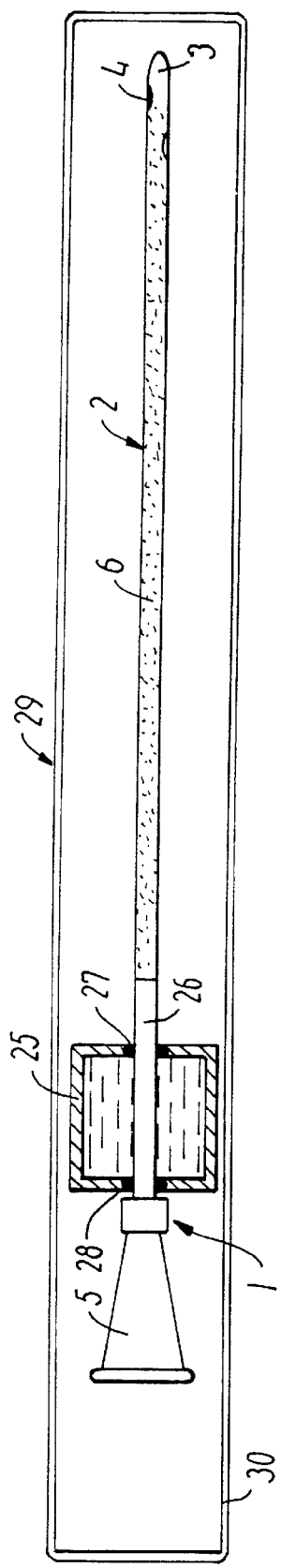
FIGS. 7 and 8 are upper plan views of a third and fourth embodiment, respectively.

In the embodiment shown in FIGS. 1 and 2 the urinary catheter assembly of the invention is intended for intermittent catherisation of the bladder of a user and comprises a urinary catheter 1 having a catheter tube 2 with cross-sectional and longitudinal dimensions suitable for introduction of the catheter through the urethra.

The catheter tube 2 extends from a distal inlet end 3, in which urine inlet openings 4 are provided, towards a proximal end, at which the catheter tube is connected with an outlet member 5 designed for connection of the catheter with a hose member (not shown) for transport of urine withdrawn from the bladder to a urine collection bag (not shown).

On a substantial part of its length from the distal end the catheter tube is, in the illustrated embodiment, coated on its external surface with a hydrophilic surface coating 6 of a kind known per se, which when cooled with a liquid swelling medium prior to use of the catheter provides an extreme low friction character of the catheter surface to enable the catheter to slide very easily through the urethra without exposing the urethral walls to any risk of damage. A hydrophilic surface layer may, however, be provided by other means and may include a catheter tube of which the active part to be located in the urethra is made entirely of a hydrophilic material.

The catheter 1 is accommodated in its entirety in a package 7 formed by two sheets 8 and 9 of a gas-impermeable thermoplastic film material such as a multiple layer film material comprising e.g. aluminium, welded together along a welding seam 10 which constitutes a joint defining a cavity 11 narrowly surrounding the catheter tube 2 and a widened end section 12 joining the cavity 11 through a transitional section 13 matching the external dimensions of the outlet or connector member 5.

The widened end section 12 forms a compartment for accommodation of the liquid swelling medium which is to be used for preparation of the catheter by activation of the low friction surface character of the hydrophilic surface coating 6. The liquid swelling medium may be any liquid suitable for this purpose and may typically comprise an isotonic or non-iotonic aqueous solution e.g. of sodium chloride or sterile water.

In order to maintain the swelling medium in liquid state until the actual preparation of the catheter the liquid swelling medium is confined in the embodiment shown in a storage body 14 which as described above may be of a spongy or gel-like material located in the compartment or end section 12.

The catheter 1 and the spongy body 14 may both be arranged in the package 7 in a sterile or antiseptic condition prior to welding the two sheets 8 and 9 of film material together to form the finished urinary catheter assembly.

Prior to the intended use of the catheter 1 the hydrophilic surface coating 6 is prepared to activate its low friction character by applying an external pressure to the end section or compartment 12 to squeeze the liquid swelling medium out from the spongy body and allow it to flow into the cavity 11. Since the welding seam 10 is arranged to provide a narrow cavity 11 around the catheter tube 2 the amount of swelling liquid needed for preparation of the hydrophilic coating 6 can be kept sufficiently low to be easily accommodated in the body 14 of spongy material. Experiments have verified that by suitable design of the cavity the amount of swelling liquid may be reduced to a volume of 2 to 50 ml, preferably 2 to 15 ml for female catheters and 5 to 30 ml for male catheters.

The period needed for preparation of the hydrophilic surface coating 6 will typically be about 30 seconds and subsequently the catheter 1 may be withdrawn from the package 7 in a ready to use condition.

To facilitate withdrawal of the catheter 1 from the package 7 the welding joint may in the transitional section 13 comprise a part forming a tear-off joint 15 permitting the entire end section or compartment 12 to be separated from the package 7, whereby the catheter 1 may as a whole be withdrawn from the package by gripping the outlet or connector member 5 only, while maintaining the catheter tube 2 in a sterile condition for insertion into the urethra with a minimum risc of infection.

As another possibility for easy withdrawal of the prepared catheter 1 from the package 7 the welding joint may, as illustrated in FIG. 3, comprise a part 10a adjacent the distal end of the catheter tube providing a peel-off joint permitting easy separation of plastic film sheets 8 and 9. Thereby, the package 7 itself will serve as an applicator to be gripped by the user to permit introduction of the catheter tube without contamination.

Due to the gas-impermeability of the package 7 it is not necessary to use a body 14 of spongy material to accommodate the liquid swelling medium. The swelling medium may be introduced in the package during the assembling operation prior to completion of the welding and will thereby immediately prepare the hydrophilic coating. The package will itself prevent the coating from drying out and preserve the low friction character of the surface coating to keep the catheter in a ready to use condition at all times. This would have the inherent advantage that no preparation step is required immediately prior to use, whereby the operation will be reduced to opening of the package 7 for immediate withdrawal of the catheter without the delay resulting from the required preparation period.

Since the preparation period is very short and the possible presence of surplus swelling liquid in the package may be uncomfortable to the user who in many situations will have to carry one or more catheter assemblies with him or her, it would frequently be preferred, however, to keep the swelling medium confined in the spongy body 14 until the moment of actual use.

In the alternative embodiments to be described in the following the catheter 1 may be of the same design as described above and will therefore not be explained in further detail.

In the embodiment shown in FIGS. 4 and 5 the package 16 is made up, in general, of a first generally tubular part 17 defining a cavity 18 which narrowly surrounds the catheter 1 and a second generally tubular part 19 defining the compartment for accommodation of the catheter outlet or connector member 5 and the spongy body 14 in which the swelling liquid is confined.

The tubular parts 17 and 19 may be integrally formed from an elongate hose-like member, one end section of which is expanded to form the compartment 19. Thereby, the package 16 may be produced from a relatively inexpensive standard hose product and the welding operation required for the embodiments in FIGS. 1 to 3 can be avoided. Such standard hose products would normally have a flexibility sufficient to allow the swelling liquid to be squeezed out of the spongy body 14 by the mere application of an external pressure to the compartment 19.

For easy withdrawal of the catheter 1 from the package 16 after preparation of the hydrophilic coating the package may include a fracture defining segment 20 provided at the transitional region between the first and second tubular parts 17 and 19 of the package.

As an alternative possibility the compartment 19 may be formed with an open proximal end closed by a removable plug-like closure member 21 which should preferably engage the spongy body 14 for removal thereof together with the closure member and provide access to the catheter outlet or connector member 5.

The embodiment shown in FIGS. 4 and 5 may be modified as shown in FIG. 6 by designing the first and second tubular parts 22 and 23, respectively, as separate parts which are detachably connected with each other by a coupling member 24 providing a gas-impermeable seal against both of the tubular parts 22 and 23.

Whereas, in the embodiments described so far the compartment for the liquid swelling medium is in direct liquid flow communication with the cavity narrowly surrounding the catheter tube, which requires the package as a whole to be made of a gas-impermeable material, the compartment for the swelling liquid may alternatively be separated from the catheter cavity in such a way that the liquid flow communication there between is not established, until preparation of the catheter is performed prior to the intended use. Thereby, only the swelling medium compartment itself needs to have walls of a gas-impermeable material preventing leakage of the swelling medium by diffusion, whereas the wall parts of the package surrounding the catheter may be made of a relatively cheaper liquid tight material.

FIG. 7 shows schematically a fourth embodiment of the catheter assembly of the invention, in which the compartment for the swelling liquid is formed by a pouch-like container 25 arranged around the proximal part 26 of the catheter tube 2 outside the hydrophilic coating 6. The catheter tube passes through the container 25 via sealed openings 27 and 28. The catheter 1 and the pouch-like container 25 are arranged together in the package 29 which may be made from two sets of plastic film material welded together in a way somewhat similar to the embodiments shown in FIGS. 1 to 3. Preferably, such a package would be designed for peel-off separation of the two sheets from the proximal end 30 to permit withdrawal of the catheter 1 by gripping the catheter outlet or connector member 5. During the withdrawal movement the catheter tube 2 will be drawn through the pouch-like container 25, whereby the swelling liquid will be applied directly to the hydrophilic coating 6.

In the container 25 the swelling liquid may be confined in a spongy material in the same way as in the embodiments described above.

Figure 8:
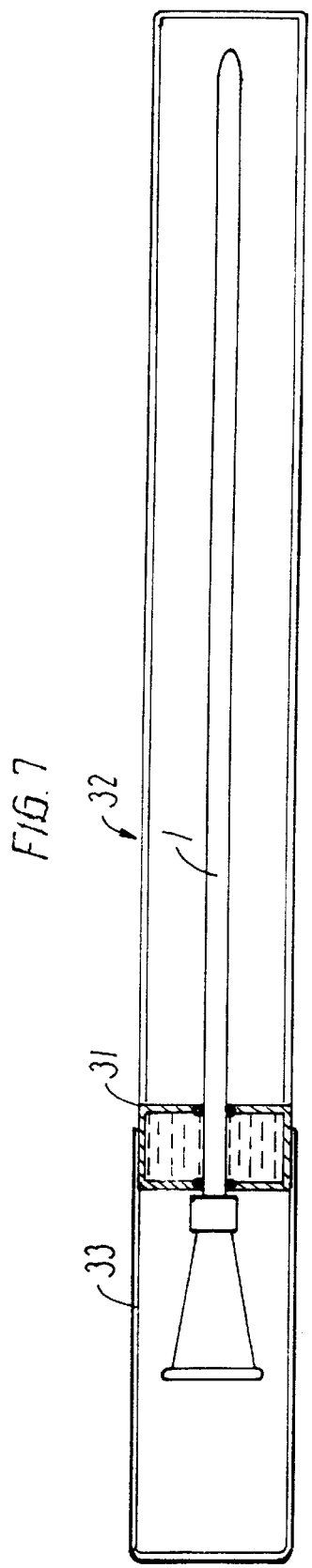

Whereas the container 25 is shown in FIG. 7 to be loosely arranged in the package 29, such a container 31 for swelling liquid may also as shown in FIG. 8 be secured to one part 32 of a generally tubular package having a second part 33 connected with the part 31 and the container 30 by a welding providing a tear-off facility to allow easy separation of the second part 33 from the package for withdrawal of the catheter 1.

Figure 9:
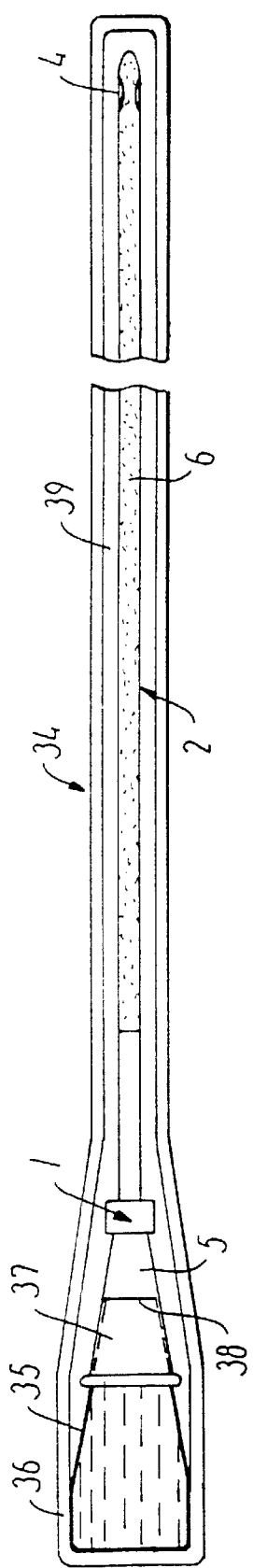
FIGS. 9 and 10 are side views of a fifth and a sixth embodiment, respectively.

In FIG. 9 an embodiment is shown with a package 34 for the catheter assembly having a general configuration similar to the package 7 for the embodiment in FIGS. 1 and 2 apart from the fact that also in this case the package need not be made of a gas-impermeable film material. The compartment for the swelling liquid is formed by a compressible ampoule 35 arranged in the widened end section 36 of package 34.

The ampoule 35 has an outlet part 37 communicating with the opening of the catheter outlet or connector member 5 and being closed by relatively faintly adhering joint 38 which by application of a pressure to the ampoule 35 without opening the package 34 will be opened to allow the swelling liquid to flow through the catheter tube 2 and the distal inlet openings 4 thereof towards the cavity 39 narrowly surrounding the part of the catheter tube 2 provided with the hydrophilic coating 6.

Figure 10:
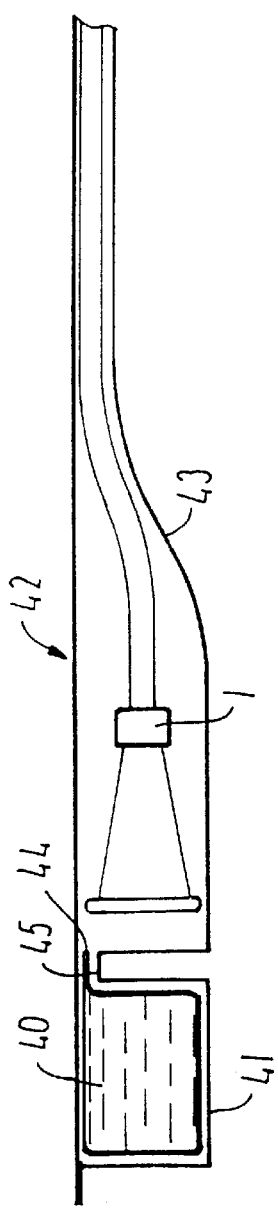

In FIG. 10 an embodiment is shown in which the swelling liquid is likewise accommodated in a compressible ampoule 40 which is arranged, however, in a separate container part 41 of a two-part container 42 the other part 43 of which defines the cavity for accommodation of the catheter 1 and is in direct liquid flow communication with the outlet part 44 of the ampoule 40. The function of the ampoule 40 in connection with preparation of the hydrophilic catheter coating 6 is generally the same as for the embodiment in FIG. 9, but as a result of the location of the ampoule outlet part 44 in the narrow flow passage 45 between container parts 41 and 43 the swelling liquid will be transferred directly through the cavity to the hydrophilic coating 6 on the external side of the catheter tube 2.

Figure 11:
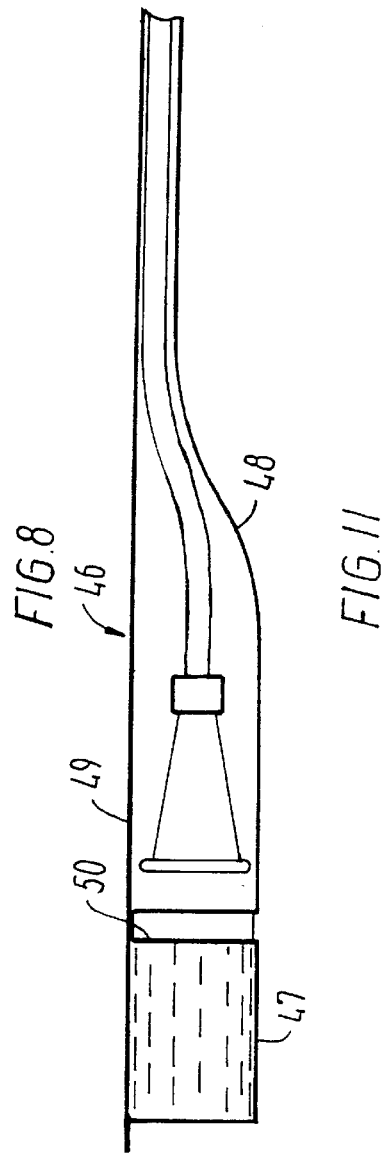
FIG. 11 is a side view of a seventh embodiment.

In FIG. 11 another design of a package in the form of a two part container 46 is shown, wherein the compartment 47 for the swelling liquid is separated from the container part 48 forming the catheter cavity by means of a common closure for the two container parts 47, 48 formed by a sheet member 49 of gas-impermeable film material. The sheet member 49 is connected with a transition part 50 of the package between container parts 47, 48 by a relatively faintly adhering peel-off joint, whereas along all other edge parts of the open container parts 47, 48 there is a relatively strong adhering joint with the common closure sheet 49. By separating the sheet member 49 from container parts 47, 48 the peel-off joint at the transition part 50 may be opened, while maintaining the joint at all other edge parts the compartment formed by container part 47 may be brought into liquid flow communication with the container part 48 accommodating the catheter 1.

Figure 12:
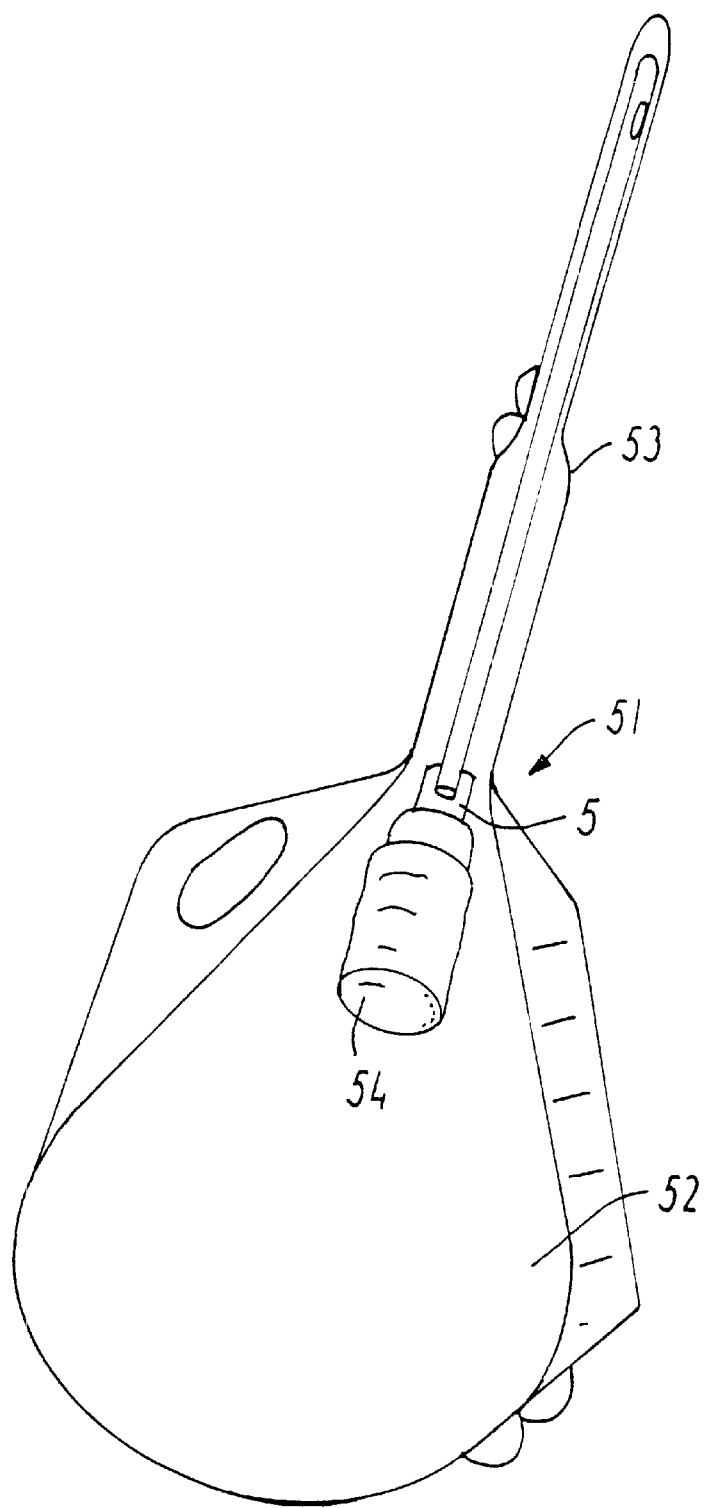
FIG. 12 is a plan view of an eighth embodiment.

In FIG. 12 a further development of the embodiment shown in FIG. 9 is illustrated in which the package 51 is formed integrally with a urine collecting bag 52. For disabled users like paraplegics or tetraplegics who as described in the foregoing may have severe difficulties in entering available toilet rooms such an integration of the urine collecting bag with the catheter package is a significant practical advantage making the use of the catheter totally independant of the availability of a toilet room. The catheter 1 is located in a relatively narrow tapering part 53 joining the collection bag 52 and the compartment for the swelling liquid is formed by a compressible ampoule 54 arranged in flow communication with the catheter outlet or connector member 5. In this case, the catheter 1 will in use not be completely removed from package 51. Instead the distal end of the tapering part 53 may be opened by peel-off separation of two plastic film sheets from which the package 51 is composed. Thereby, the catheter 1 may after preparation of the hydrophilic coating be introduced by an operation similar to the one described above for the embodiment in FIG. 3.

Due to the desirability of limiting the amount of swelling liquid to be contained in the swelling liquid compartment in those embodiments where the swelling liquid is transferred directly through the cavity narrowly surrounding the catheter tube 2 to the hydrophilic coating 6, i.e. without having to flow internally through the catheter tube 2 and through the catheter inlet openings 4, the catheter may be provided with means preventing the swelling liquid from getting into contact with internal or external surface parts of the catheter 1 not provided with the hydrophilic coating 6, during the period needed for preparation of the hydrophilic coating to activate its low friction character. Such means may in a simple manner comprise the application of a film layer 55 of a material soluble by the actual swelling medium to said internal or external surface parts.

Figure 13:
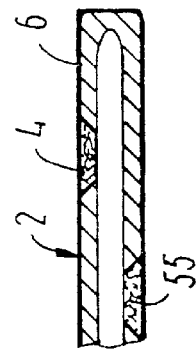
FIG. 13 illustrates a part of a catheter provided with means to reduce the amount of liquid swelling required for activation of a hydrophilic surface coating.

As shown in FIG. 13 this may be done in the most simple way by application of such film layers 55 over the catheter inlet openings 4. Thereby, substantially the entire quantity of swelling medium will be effectively used for the preparation of the hydrophilic surface coating.

Figure 14:
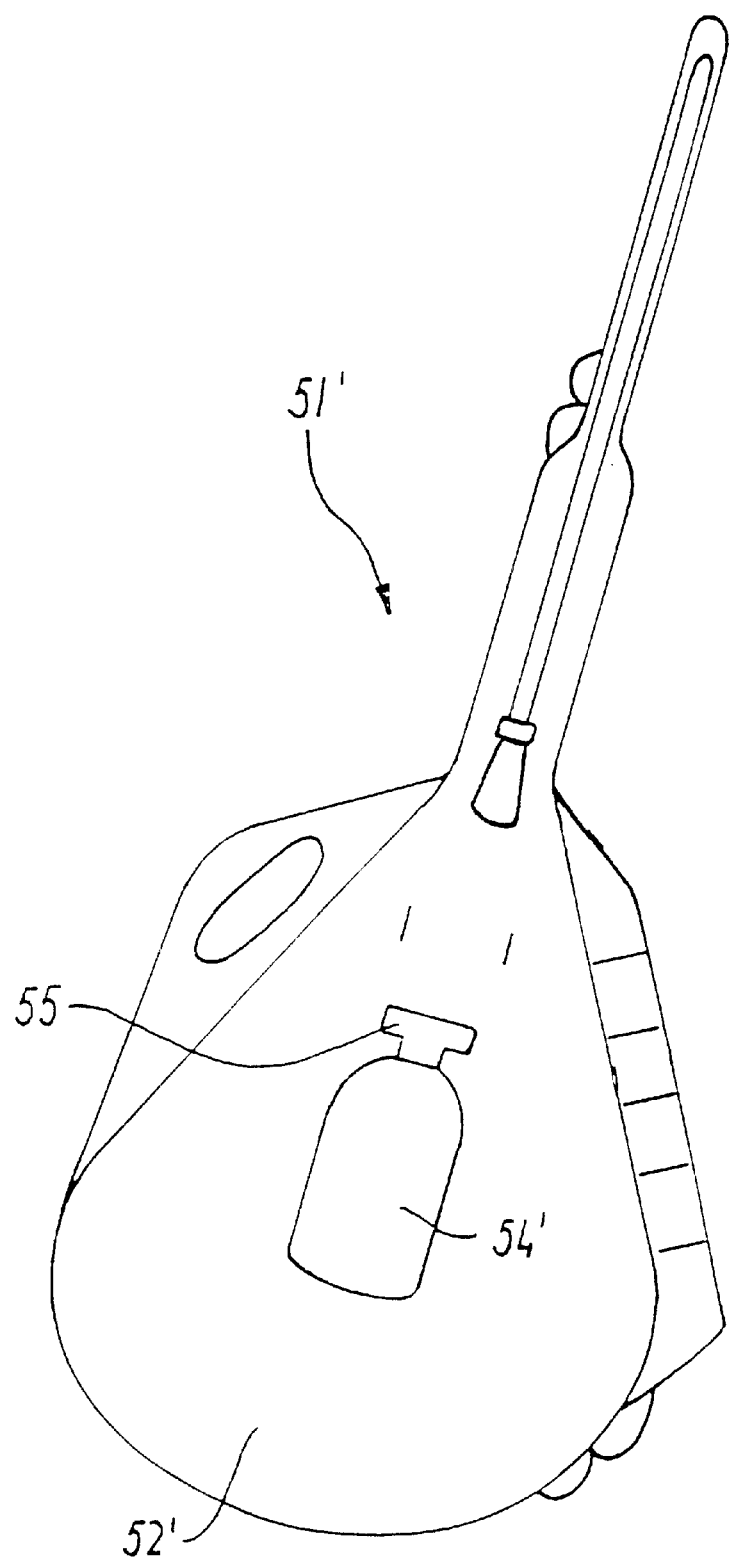

In FIG. 14 a modification of the embodiment shown in FIG. 12 is shown, in which a compressible ampoule 54' is loosely arranged in the urine bag part 52' of the catheter package 51'. At one end, the ampoule 54' is closed by a breakable closure device 55, which can be broken off by manipulation through the walls of the bag 52'.

Figure 15:
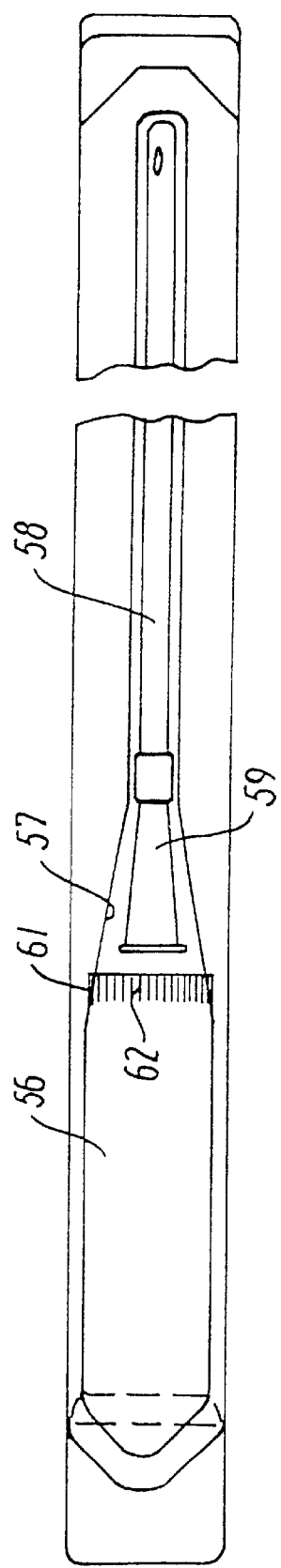
Figure 16:
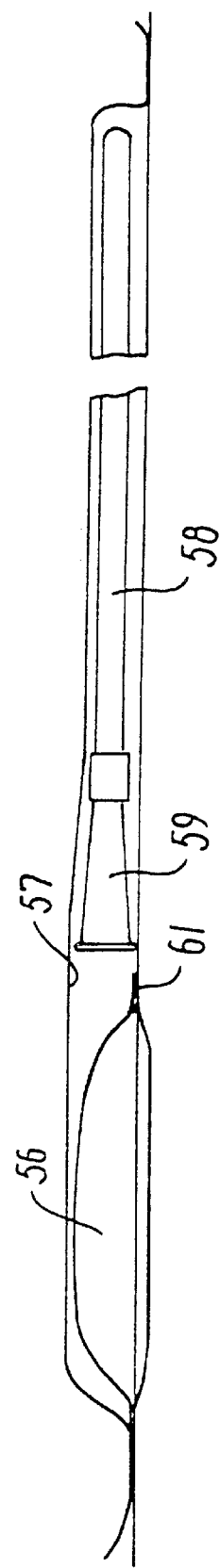

In FIGS. 15 and 16, an embodiment is shown, in which the compartment for the liquid swelling medium is formed as a rupturable pouch 56 and is arranged in the cavity 57 for the catheter 58 in liquid flow communication with an outlet member 59 connected with the catheter 58 at the proximal end thereof. An outlet part 61 of the ampoule is provided at the end of the pouch facing the catheter outlet member 59. The outlet part 61 is closed by a rupturable closure in the form of a welding 62 providing a relatively faint joint, which will be ruptured by applying pressure on the pouch 56 by squeezing without opening the catheter package. This embodiment is very easy to operate by a user having poor dexterity.

In the embodiments to be described in the following the compartment for the swelling medium is formed by a relatively rigid container arranged within the catheter package in extension of an outlet member provided at the proximal catheter end.

Figures 17, 18:
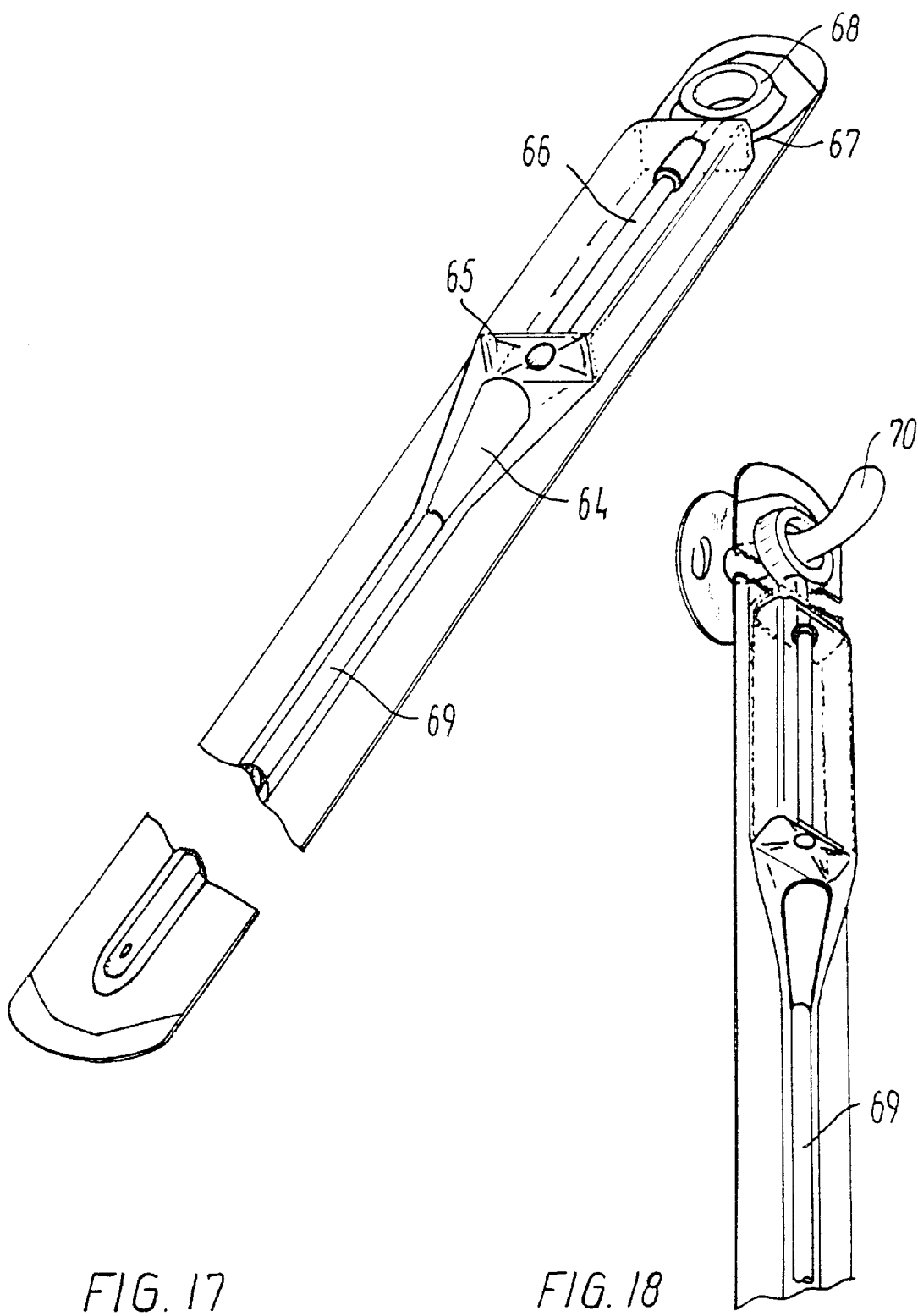

In the embodiment shown in FIGS. 17 and 18 this container is formed as a relatively flat box 63 which at an end facing the catheter outlet member 64 is closed by a closure in the form of a rupturable membrane 65, connected with an operating device permitting rupturing of the membrane without opening the catheter package.

In the embodiment shown this operating device comprises a rod-like member 66 connected with the membrane 65 and extending throughout the length of the box-shaped container 64 and through an end wall 67 of the catheter package to a gripping member 68, which can be operated by the user to rupture the membrane 65, whereby the swelling medium content in the container 63 will flow through the catheter 69 in the manner described in the foregoing.

As illustrated in FIG. 18, a particular easy operation may be obtained, if the gripping member 68 is formed as a ring, which will allow the catheter package as a whole to be hung on a hook 70 or similar device, which is normally available in a toilet or bathroom. Operation of the package to effect treatment of the hydrophilic surface part of the catheter 69 may then be effected by pulling the entire package hung on such a hook.

In the modification illustrated in FIGS. 19 and 20, a compartment in the form of a flat box-like container 71 somewhat similar to the container 63 shown in FIGS. 18 and 19, is formed with an open end 72 facing the catheter outlet member 73. A sealing closure between the compartment accomodating the liquid swelling medium and the catheter cavity 74 of the package is obtained by means of an external clamp 75 squeezing the walls of the catheter package 76 together. Thereby, the treatment of the hydrophilic surface part of the catheter 77 can simply be effected by removing the clamp 75.

In the embodiment shown in FIGS. 21 and 22, a rigid container compartment 78 for the liquid swelling medium has a generally conical shape and is formed integrally with the catheter outlet member 79 in extension thereof. Between the outlet member 79 and the container 78 a fracture region 80 is provided allowing the container 78 to be easily broken off from the catheter outlet member 79, whereby a liquid-tight closure in the form of a membrane 80*a* closing the end of the container 78 facing the outlet member 79 will automatically be ruptured to allow the content of liqid swelling medium in the container 78 to flow through the catheter 81 to effect treatment of the hydrophilic surface part thereof.

In FIGS. 23 and 24, an embodiment is illustrated in which an ampoule 82 accomodating the liquid swelling medium is arranged within the catheter package in extension of the catheter outlet member 83. The ampoule 82 is connected with an operation member 84 through a connecting assembly 85 comprising a plug-like closure member 87 formed integrally with the operation member 84 and pivotally connected with a collar member 86 secured to the ampoule 82, whereby the ampoule 82 can be pivoted with respect to the operation member 84, by gripping the latter together with the catheter outlet member without opening the package, to assume the position shown in dashed lines, whereby the closure 87 will be removed from the ampoule to allow the liqud swelling medium to flow out and effect treatment of the hydrophilic surface part of the catheter 88.

In FIG. 25, a modification of the embodiment in FIGS. 23 and 24 is shown, in which an ampoule 89 for the liquid swelling medium is closed by a rupturable membrane 90 and is connected with an operation member 92, which in the package is located opposite the end of the catheter outlet member 91 and is formed, on its inner side facing the membrane 90, with a rupturing projection 93. The operation member 92 is arranged to be displaceable on a neck part of the ampoule 89 and is normally held thereon in an inactivated position, in which the rupturing projection 93 is removed from the membrane 90, by means of projecting pins 94 engaging a recess 94a formed in the operation member 92. The membrane 90 can be ruptured by the rupturing projection 93 without opening the catheter package by operating the catheter outlet member 91 to push the operation member 92 with respect to the ampule neck part 94.

In a further modification illustrated in FIG. 26, an ampoule 95 closed by a rupturable membrane 96 is connected with the catheter outlet member 97 by an operation member comprising two pitally interconnected parts 98 and 99 connected with outlet member 97 and ampoule 95, respectively. Operation member part 98 is formed with a rupturing projection 100 for membrane 96. Activation of the ampoule 95 by rupturing the membrane 96 may be effected without opening the catheter package by pivoting the ampoule 95 with respect to the catheter outlet member 97 from the supply position shown in solid lines, in which the ampoule 95 extends parallel with respect to the catheter, to the activation position shown in dashed lines.

Figures 27, 28:
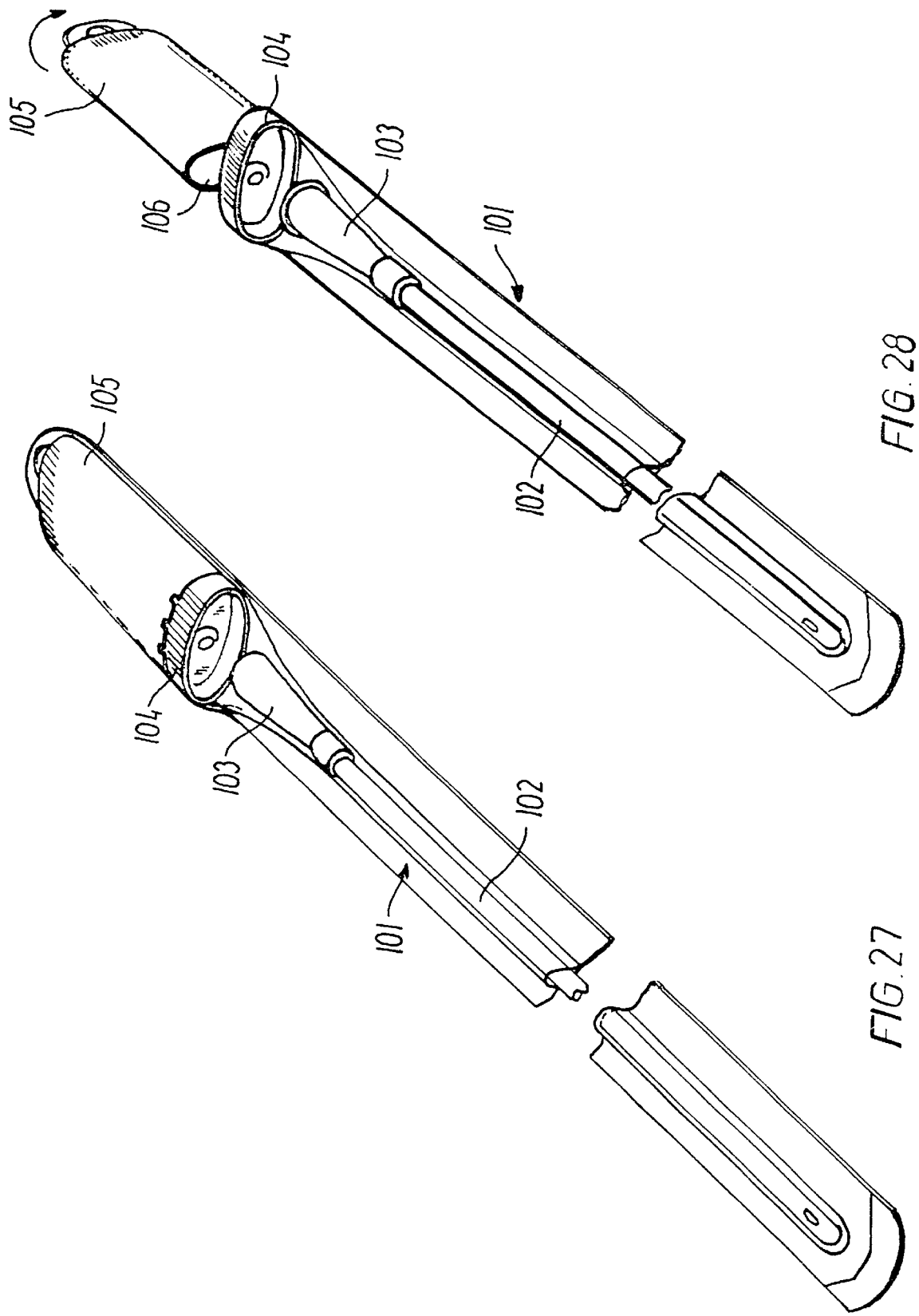

In the embodiment shown in FIGS. 27 and 28, the catheter package 101 providing the cavity for the catheter 102 is closed at the end opposite the catheter outlet member 103 by a rigid end wall 104 and the compartment for the liquid swelling medium is formed by an external rigid container 105 arranged outside the package itself against the end wall 104. As illustrated, the container 105 is arranged to be turnable through approximately 90° with respect to the end wall 104 to bring liquid outlet and inlet openings provided in an end wall 106 of the container 105 facing the rigid end wall 104 and in the latter end wall, respectively, into liquid flow alignment, whereby the content of liquid swelling medium in the ampoule 105 will be transferred to the catheter package to effect treatment of the hydrophilic surface part of he catheter 102.

Whereas different embodiments of ready to use urinary catheter assemblies according to the invention have been described in the following the invention is not limited to the specific characteristics of these embodiments, but will include numerous modifications without departing from the scope of the patent claims.

Thus, a catheter assembly according to the invention may well comprise a number of catheters packed in individual packings each comprising a compartment for swelling liquid and all arranged in a common package providing the prescribed gas impermeability.

What is claimed is:

1. A urinary catheter assembly comprising:
    a urinary catheter having on at least a part of its surface a hydrophilic surface layer, to produce a low-friction hydrophilic surface coating on said catheter when treated with a liquid swelling medium prior to use of said catheter;
    a catheter package made throughout of a gas impermeable material to form a cavity for accommodation of said catheter, said cavity receiving said catheter and said liquid swelling medium during a manufacturing assembly operation so as to provide a ready-to-use catheter assembly in which said liquid swelling medium is in direct liquid flow communication with the cavity;
    said liquid swelling medium having been introduced into said package during said assembly operation, and said package thereafter preventing said hydrophilic surface coating from drying out, thereby permitting long-time preservation of said low-friction surface coating of said catheter in a pretreated form.

2. The urinary catheter assembly as claimed in claim 1, wherein said catheter package includes a bag communicating with the catheter for collection of urine.

3. The urinary catheter assembly as claimed in claim 1, wherein said catheter package is formed from two sheets of gas impermeable film material connected to each other by a gas impermeable joint defining said cavity for accommodating the catheter.

4. The urinary catheter assembly as claimed in claim 3, wherein said catheter package is of a general elongate shape with said joint arranged to define said cavity to accommodate said catheter in a substantially linear orientation.

5. The urinary catheter assembly as claimed in claim 3, wherein said joint is arranged to provide said cavity with a cross-section narrowly surrounding said catheter.

6. The urinary catheter assembly as claimed in claim 3, wherein a compartment is provided at one end of said cavity.

7. The urinary catheter assembly as claimed in claim 6, wherein a liquid swelling medium is confined in a storage body arranged in said compartment.

8. The urinary catheter assembly as claimed in claim 7, wherein said catheter package includes a transitional section between said cavity and said compartment for accommodation of a proximal outlet member of said catheter.

9. The urinary catheter assembly as claimed in claim 6, wherein said package comprises a first generally tubular part defining said cavity to narrowly surround said catheter and a second generally tubular part defining said compartment.

10. The urinary catheter assembly as claimed in claim 9, wherein said first and second tubular parts are integrally formed from an elongate hose member, one end section of which is expanded to constitute said second tubular part.

11. The urinary catheter assembly as claimed in claim 9, wherein a liquid swelling medium is confined in a storage body arranged in said second tubular part.

12. The urinary catheter assembly as claimed in claim 10, wherein a fracture defining segment is provided in said hose member in a transitional region between first and second tubular parts to allow separation of said compartment from said cavity for withdrawal of said catheter.

13. The urinary catheter assembly as claimed in claim 10, wherein said first and second tubular parts are separate parts which are detachably connected with each other to allow separation of said compartment from said cavity for withdrawal of said catheter.

14. The urinary catheter assembly as claimed in claim 3, wherein said joint is a welding joint.

15. The urinary catheter assembly as claimed in claim 14, wherein said welding joint comprises at least a part at an end of said package providing a peel-off joint to separate said sheets from each other for withdrawal of said catheter from said package.

16. The urinary catheter assembly as claimed in claim 1, wherein said liquid swelling medium is selected from the group consisting of an aqueous solution, an isotonic aqueous solution, an isotonic aqueous solution of sodium chloride, and sterile water.

17. A urinary catheter assembly comprising:
   a urinary catheter having on at least a part of its surface a hydrophilic surface layer which produces a low-friction hydrophilic surface coating on said catheter when treated with a water-based liquid swelling medium prior to use of said catheter;
   a catheter package made throughout of a gas impermeable material to form a cavity for accommodation of said catheter, said cavity receiving said catheter and said water-based liquid swelling medium during a manufacturing assembly operation so that said hydrophilic surface coating is treated during said manufacturing assembly to form a ready-to-use catheter assembly in which said water-based liquid swelling medium is in direct liquid flow communication with the cavity, said package thereafter preventing said hydrophilic surface coating from drying out to provide long-time preservation of said low-friction surface coating of said catheter in a pretreated form.

18. The catheter assembly as set forth in claim 17, wherein said water-based liquid swelling medium is sterile water.

19. The catheter assembly as set forth in claim 17, wherein said water-based liquid swelling medium is an aqueous solution.

20. The catheter assembly as set forth in claim 13, wherein said aqueous solution is an isotonic aqueous solution.

21. The catheter assembly as set forth in claim 17, wherein said aqueous solution is an isotonic aqueous solution of sodium chloride.

* * * * *